United States Patent [19]

Wells et al.

[11] Patent Number: 4,999,162
[45] Date of Patent: Mar. 12, 1991

[54] HIGH TEMPERATURE FLAME JET FOR GAS CHROMATOGRAPHY

[75] Inventors: Gregory J. Wells, Suisun; John R. Berg, Davis, both of Calif.

[73] Assignee: Varian Associates, Inc., Palo Alto, Calif.

[21] Appl. No.: 237,266

[22] Filed: Aug. 26, 1988

[51] Int. Cl.⁵ ............................................. G01N 30/68
[52] U.S. Cl. ........................................ 422/54; 422/89; 436/155; 73/23.4; 55/386; 55/67
[58] Field of Search ................. 422/54, 89; 436/155; 73/23.1; 55/386, 67; 210/198.2

[56] References Cited

U.S. PATENT DOCUMENTS

| | | | |
|---|---|---|---|
| 3,372,000 | 3/1968 | Gallaway et al. | 422/54 |
| 3,585,003 | 6/1971 | Scolnick. | |
| 3,954,651 | 5/1976 | Donike | 55/67 |
| 4,182,740 | 1/1980 | Hartman et al. | 422/54 |
| 4,798,805 | 1/1989 | Issenmann | 422/54 |

FOREIGN PATENT DOCUMENTS 1451795  10/1976  United Kingdom .

OTHER PUBLICATIONS

Stephen D. Nogare, Richard S. Juvet, Gas-Liquid Chromatography Theory & Practice, pp. 144–146, 1962, Interscience Publishers, New York-London.

Primary Examiner—Robert J. Warden
Assistant Examiner—Abanti B. Singla
Attorney, Agent, or Firm—Stanley Z. Cole; David Schnapf

[57] ABSTRACT

A flame detector comprising a ceramic flame jet for use in a high temperature gas chromatography system is disclosed. The interior volume of the flame jet is fabricated of a highly inert ceramic material so that sample eluting from the end of a gas chromatography column located within the interior volume of the flame jet does not contact any metallic surface en route to the flame. By avoiding sample contact with metallic surfaces, interferences which are prone to occur at high temperature, such as peak tailing, are avoided. In a further aspect the flame detector is treated with a silylating reagent to further passivate the surfaces which may affect the sample.

19 Claims, 3 Drawing Sheets

HIGH TEMPERATURE FLAME JET FOR GAS CHROMATOGRAPHY

BACKGROUND OF THE INVENTION

This invention is in the field of gas chromatography and particularly relates to flame detectors used in gas chromatography systems for analyzing the sample eluting from the chromatography column after separation by the column into its constituent components.

One type of flame detector, the flame ionization detector, is a well known and commonly used device for analyzing the output of a gas chromatograph. Examples of flame ionization detectors are found in U.S. Pat. Nos. 3,585,003 and 4,182,740 which are coassigned with the present invention. Flame ionization detectors are particularly useful for analyzing organic compounds.

In a flame ionization detector, sample exiting a gas chromatography column, where it is separated into its component compounds, is combusted in an air/hydrogen flame. Typically, the exit end of a gas chromatography column and a source of hydrogen fuel are located within a hollow flame jet and exit through an orifice where the mixture encounters an air flow which provides oxygen to support a flame. Ions created by the breakdown of the sample in the flame are transported by gas flow past an electrode, normally referred to as the collecting electrode. The collecting electrode is connected to a current measuring device where changes in ion current, corresponding to changes in the sample mixture, are read. In many commercial devices another electrode within the detector is polarized with a DC voltage of several tens to several hundreds of volts. Typically, a metal flame jet is used as this "polarizing electrode".

One problem associated with using metal flame jets is that the metal surfaces are not very inert at high temperatures and can interfere with the performance of the detector by adsorbing or otherwise affecting the sample eluting from the end of the chromatography column. This problem may be mitigated by locating the end of the column near the orifice of the flame jet, thereby minimizing the amount of metal surface likely to be contacted by the sample. However, this approach does not fully eliminate sample contact with the internal metal surfaces of the flame jet.

A trend in gas chromatography has been towards higher temperature operation. It is now possible to obtain a commercial gas chromatography system, the Varian Model 3410, which operates at temperatures as high as 500° C. This trend has led to the greater use of aluminum clad chromatography columns instead of the polyimide clad columns previously employed, since polyimide cladding is unable to survive temperatures higher than approximately 350° C. Using aluminum, which is a good electrical conductor, as the cladding material, however, dictates that the column end not be placed in close proximity to the orifice of a metal flame jet because of the possibility of electrical shorting.

Another solution to the problem encountered when the sample contacts metal surfaces is the use of a flame jet constructed of quartz, with either a metallic coating on the outer surface of the flame jet to form the polarizing electrode or a separate polarizing electrode located in proximity to the flame. However, this solution has not proved satisfactory for high temperature operation because microscopic particles of the quartz tend to break off during operation of the detector and enter the flame. The release of microscopic quartz particles causes sharp noise spikes, the magnitude and frequency of which are a function of a number of variables including the fuel gas ratios. It is believed that the microscopic particles are formed when thin sections of the quartz near the orifice of the jet are heated by the flame and undergo a phase transition resulting in a higher bulk volume and high localized stresses. It has been observed that the noise problems associated with quartz flame tips increase as the temperature of the system is increased.

Accordingly, it is an object of this invention to provide a flame jet for use in a flame detector in a gas chromatography system which forms a polarizing electrode and which is highly physically and chemically inert.

Another object of this invention is to provide a flame jet for use in a flame ionization detector in a gas chromatography system which provides high performance at temperatures as high as 500° C.

SUMMARY OF THE INVENTION

The novel design of the present invention comprises a flame jet constructed largely of high purity alumina or other suitable ceramic material and which further comprises a metallic outer surface enabling the flame jet to act as a polarizing electrode. High purity alumina is used in the preferred embodiments because it is highly inert and has a coefficient of expansion which is very close to that of the metal, i.e., Kovar ® (a registered trademark of Carpenter Technology Corp.), used in the preferred embodiment for the electrode surface and for mounting the flame jet. In the present design the entire interior structure of the flame jet between the column end and the jet orifice, i.e., the portion of the interior which is likely to come into contact with sample eluted from the end of the chromatography column, is constructed of ceramic material in order to avoid any contact between the sample and a metallic surface.

In a further aspect of a preferred embodiment of the present invention the flame jet is further treated by a silylating process to further improve its chemical inertness.

DETAILED DESCRIPTION

Figure 1:
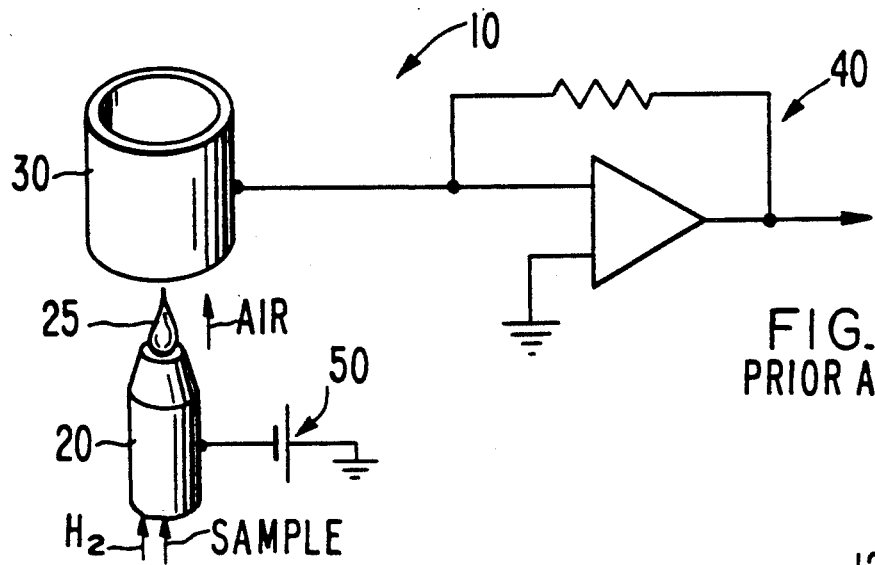
FIG. 1 is a schematic representation of a flame ionization detector wherein the flame jet serves as a polarizing electrode.

FIG. 1 shows a schematic view of a typical flame ionization detector 10 for use in analyzing the output of a gas chromatograph. A flame jet 20 supports a flame 25 at an orifice. Flame 25 is formed by the combustion of hydrogen in air. The hydrogen is introduced into the detector from within the interior of the flame jet 20 while the air is introduced outside the flame jet 20. The oxygen in the air mixes with the hydrogen exiting the flame jet 20 through an orifice in its tip supporting the flame 25. Well known means, not shown, are provided for igniting the air hydrogen mixture.

Sample eluting from the end of a gas chromatography column is released within the flame jet 20 and is swept by the hydrogen through the orifice into the flame. Compounds in the sample stream are combusted in the flame 25 producing ions which are swept by the flowing gasses past a collector electrode 30. Electronic measuring means 40 measure changes in the ion current and these measurements are transmitted to a recording means (not shown). Various types and designs for the electronic measuring means 40 and the recording means are well known in the art and need not be discussed further. In prior art devices, flame jet 20 has typically been constructed of a metal, with the tip of the flame jet 20 serving as a polarizing electrode by virtue of an electrical connection to a voltage source 50.

Figure 2:
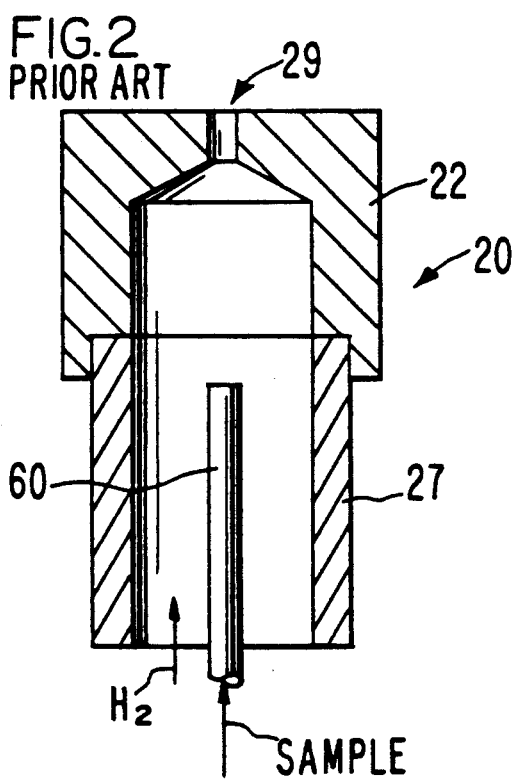
FIG. 2 is a cross sectional view of a prior art flame jet used in a flame ionization detector.

FIG. 2 shows a cross-sectional view of a flame jet 20 of the type known in the prior art. A metal tip 22 is attached to an insulating tube 27 to electrically isolate the tip. In a typical commercial embodiment, metal tip 22 is made of Kovar ® (i.e., an alloy of cobalt, iron and nickel). Insulating tube 27 is made of alumina. Both Kovar ® and alumina are able to readily withstand high temperature operation and have quite similar coefficients of expansion. Metal tip 22 is connected to a voltage source (as shown in FIG. 1) and serves as a polarizing electrode. Chromatography column 60 terminates within the interior of flame jet 20 so that separated sample is released into the volume and swept to the flame jet orifice 29 by a stream of hydrogen fuel also released with the flame jet 20. As described above, the sample and hydrogen fuel then exit the flame jet 20 through the orifice 29 and into the flame.

Many metals, including Kovar ®, although active in their pure state quickly form a relatively stable and inert oxide surface layer when exposed to the oxygen in air. It is believed that, in prior art flame jets, this oxide layer has acted to prevent interferences caused by the sample coming into contact with an active metal surface. However, when operating a gas chromatography system at high temperatures, e.g., above 350° C., the oxide layer is reduced by the hydrogen gas flowing on the inside of the flame jet leaving a surface of active metal which interferes with the sample analysis. An example of such an interference is the adsorption and later desorption of sample causing a "tail" on a chromatographic peak. It should be understood that in high temperature gas chromatography the entire flame jet must be maintained at an elevated temperature to prevent sample condensation within the flame jet.

While it is clear that contact between the sample and the metal flame tip 22 can be minimized by positioning the end of column 60 close to orifice 29, a distance between these must be maintained when using aluminum clad columns to avoid any shorting of the aluminum to the polarized metal flame jet tip 22. As noted above, it has become common to use such aluminum clad columns when operating at temperatures above 350° C. because polyimide cladding cannot tolerate such temperatures. In any case, contact with even a relatively small metallic surface can cause undesirable peak tailing and impaired system performance. Thus, for example, use of an insulating member between the column end and a metal flame tip would not eliminate the problem, even if it would allow closer proximity between the column 60 end and the flame tip orifice 29.

Figure 3:
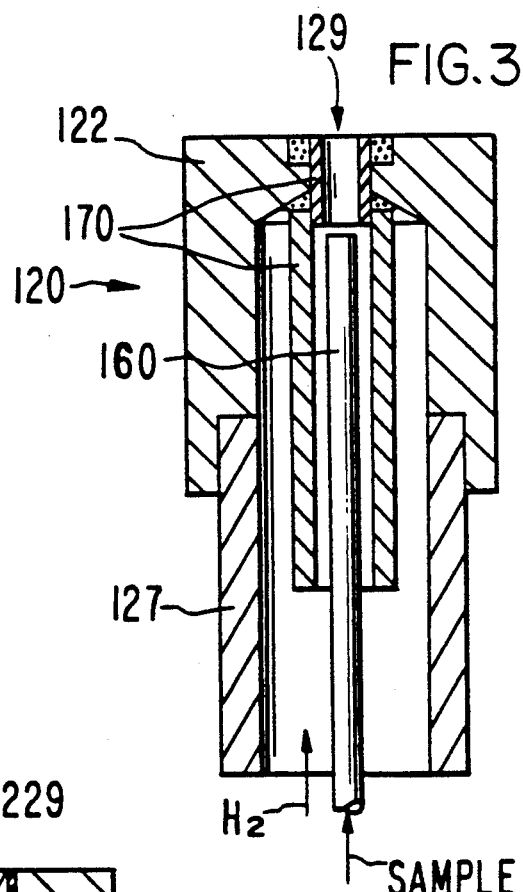
FIG. 3 is a cross sectional view of a flame jet of the present invention.

One embodiment of the present invention is shown in FIG. 3 wherein structural elements corresponding to those in FIGS. 1 and 2 are similarly numbered with the addition of 100. Thus, flame jet 120 comprises metal flame tip 122 and alumina insulating member 127. Gas chromatography column 160 terminates within the interior space of flame jet 120. However, in contrast to the flame jet described above in connection with FIG. 2, ceramic tubular elements 170 are cemented to the metal flame tip 122 providing a path for the sample to flow from the end of column 160, through the orifice 129 and into the flame (not shown) without contacting any metal surface.

In the preferred embodiment of the present invention ceramic elements 170 are made of alumina and the metal flame tip 122 is made of Kovar ®. Again, this combination of materials works well together due to their abilities to withstand high temperature and the similarity of their coefficients of expansion. For modern high temperature operation it is essential that the ceramic material which is chosen for elements 170 be highly chemically inert at temperatures as high as 500°. Thus, while alumina is readily available in various degrees of purity, in the preferred embodiment of the present invention the alumina used should be at least 95% pure to provide a high level of inertness. If substituting another ceramic material one should carefully evaluate the chemical activity of the material at high temperatures.

In the preferred embodiment of the invention as depicted in FIG. 3, the cement used to bond ceramic tubular elements 170 to the metal flame tip 122 is a high purity alumina cement. Such cement is readily available and can be purchased, for example, as from Cotronics Corporation of Brooklyn, N.Y., under the trade designation Ceramic Adhesive Type 989.

Figure 4:
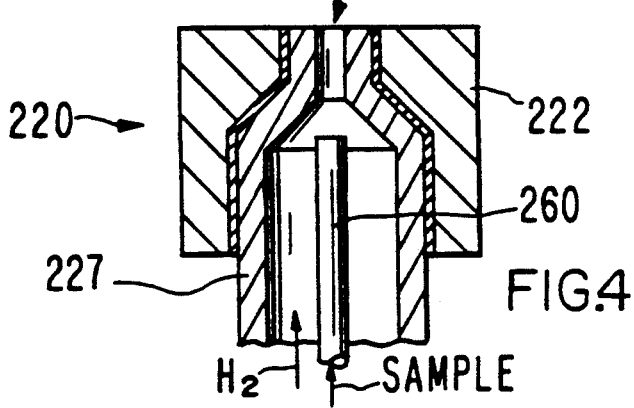
FIG. 4 is an alternate embodiment of a flame jet of the present invention.

Another embodiment of the invention is depicted in FIG. 4. wherein structural elements corresponding to those in FIGS. 1 and 2 are similarly numbered with the addition of 200. This embodiment comprises an integral ceramic member 227 which is brazed directly to metal tip 222. It should be noted that another advantage of using Kovar ® for the metal portions of the flame jet lies in the ease with which it can be brazed to ceramic material, especially alumina. Ceramic member 227 is machined to the proper shape for nesting within metal tip 220. Again, in this embodiment the sample gas is released from the end of a chromatography column 260 within the interior volume of ceramic member 227 and is swept by the hydrogen fuel into the flame (not shown) via orifice 229. The sample does not contact any metal surface as it travels to the flame.

It should be noted that metal elements 22, 122 and 222, in FIGS. 2, 3, and 4, respectively, are connected to a DC polarizing voltage via an electrical connection (as is shown schematically in FIG. 1). In both the FIG. 3 and FIG. 4 embodiments the end of an aluminum clad column can be positioned quite close to the exit orifice 129 or 229 of the flame jet 120 or 220, respectively, without fear of electrical shorting. Positioning the column close to the orifice reduces contact between the sample and the surface within the flame jet. Even though the interior surface of the flame jet is made is made highly inert when practicing the present invention, it is still desirable to bring the column end as close as possible to the flame jet orifice to minimize dead volume and to mitigate the possibility of sample fragmentation due to pyrolysis on the heated interior surfaces of the flame jet. This latter problem is of greater significance when operating at very high temperatures.

In a further aspect of the present invention, it has been found that treating the flame jet with a silylating reagent improves the performance by further passivating the chemical activity of the flame jet. The silylating treatment may be accomplished by passing of an appropriate reagent such as dichlorodimethyl silane or N,O-bistrimethylsilyl-trifluoroacetemide (BSTFA) through the flame jet at temperatures in excess of 400° C.

Figure 5:
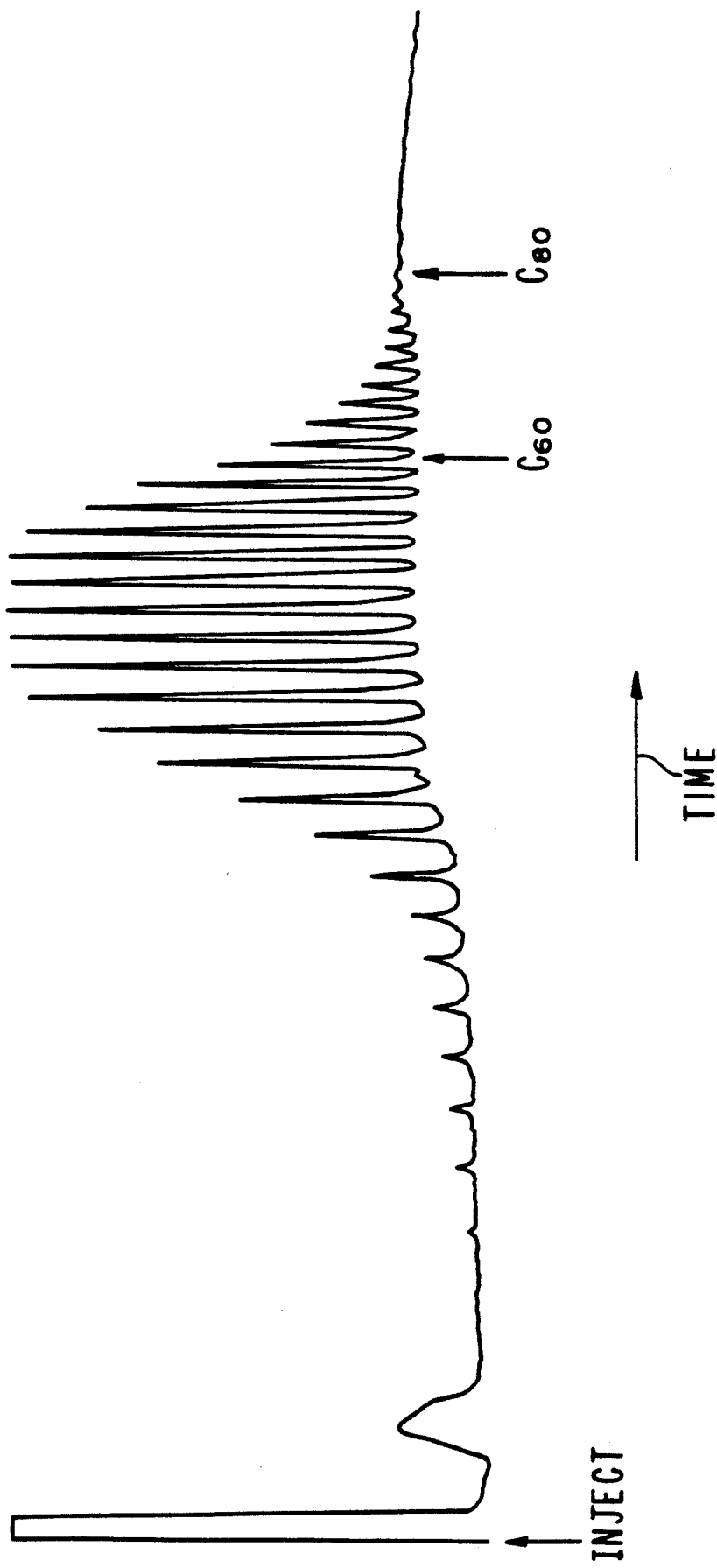
FIG. 5 is a chromatogram of Polywax 655 made using a prior art flame ionization detector.
Figure 6:
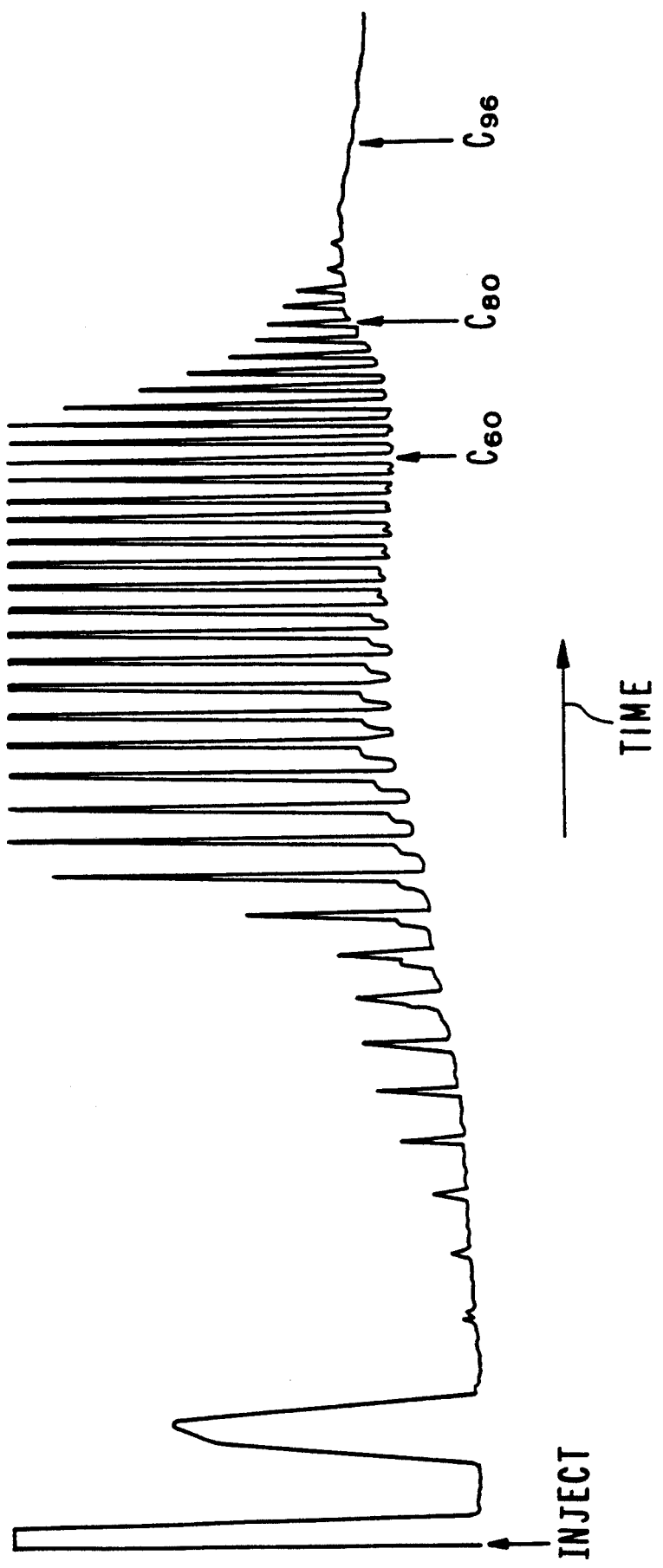
FIG. 6 is a chromatogram of Polywax 655 made under identical conditions using a flame ionization detector of the present invention.

The advantages of this invention can be seen by referring to FIGS. 5 and 6 representing chromatograms run under identical conditions except that the FIG. 5 chromatogram was recorded using a flame ionization detector comprising a prior art all-metal flame jet, while the FIG. 6 chromatogram was recorded using a flame ionization detector comprising a flame jet in accordance with the present invention. Both chromatograms, run using a 0.53 mm aluminum clad column in a Varian 3410 GC system, represent the separation of Polywax 655, which is composed of primarily even polyethylene polymers that extend beyond 100 carbon units. In both figures the horizontal axis represents increasing time and the vertical axis increasing peak height. The scaling of the axes is the same in both chromatograms, i.e., one unit along the horizontal axis represents the same time increment in both figures.

In comparing the two chromatograms it is evident that the ceramic flame jet produces peaks with better shape, i.e., the peaks are sharper, with no tailing and much better resolution. Moreover, the FIG. 6 chromatogram shows improved sensitivity due to diminished sample loss in the flame jet. The improvement appears to be in the range of a factor of 5-10, although many of the peaks in the FIG. 6 chromatogram are off scale. In the FIG. 5 chromatogram there are no peaks beyond C-80; while the FIG. 6 chromatogram shows peaks up to C-96.

Since many changes could be made in the above construction and many apparently widely different modifications and embodiments of this invention can be made without departing from the scope thereof, it is intended that all matter contained in the above description or shown in the accompanying drawings shall be interpreted as illustrative and not in a limiting sense. In particular, while the preferred embodiments of the invention has been described in the context of a flame ionization detector, the advantages of the invention have clear application to other types of flame detectors used in gas chromatography such as the thermionic specific detector.

What is claimed is:

1. A flame detector for use in a gas chromatography system, comprising:
    a flame jet apparatus having a hollow interior adapted for containing the sample eluting end of a chromatography column and an interior surface, the portion of the interior surface of said flame jet apparatus which is contacted by the sample eluting from the end of the chromatography column being made of a highly inert ceramic material which has been treated by contacting the interior surface with a silylating reagent at an elevated temperature.

2. The flame detector of claim 1 wherein the silylating treatment comprises passing dichlorodimethyl silane or N,O-bis-trimethylsilyl-trifluoroacetemide (BSTFA) through the flame jet at temperatures in excess of 400° C.

3. A flame ionization detector for use in gas chromatography, comprising:
    a flame jet apparatus having an orifice for supporting a flame in the vicinity of the orifice, the flame jet apparatus comprising a hollow interior space adapted to receive the sample-eluting end of a gas chromatography column and a metallic exterior surface adjacent to the orifice;
    voltage means for maintaining the metallic exterior surface at a constant elevated voltage so that the surface serves as a polarizing electrode;
    means for releasing a flow of hydrogen fuel gas within the interior space of the flame jet whereby the flow of fuel gas sweeps sample eluting from the end of the gas chromatography column out of the orifice and into the flame;
    a collecting electrode positioned adjacent to the flame jet apparatus attached to means for measuring changes in ion current which occur as sample is combusted in the flame;
    the interior surfaces of the flame jet apparatus which may contact the sample eluting from the gas chromatography column being made of a highly inert ceramic material which has been treated by contacting the interior surface with a silylating reagent at an elevated temperature.

4. The flame detector of claim 13 wherein the silylating treatment comprises passing dichlorodimethyl silane of N,O-bis-trimethylsilyl-trifluoroacetemide (BSTFA) through the flame jet at temperatures in excess of 400° C.

5. A method of improving the performance of a gas chromatography flame detector comprising treating the interior surfaces of the detector with a silylating reagent to chemically passivate the interior surfaces.

6. The method of claim 5 wherein the silylating treatment comprises passing dichlorodimethyl silane or N,O-bis-trimethylsilyl-trifluoroacetemide (BSTFA) through the flame jet at temperatures in excess of 400° C.

7. A gas chromatography system comprising:
    a fused silica chromatography column, adapted to withstand temperatures as high as 400° C., for separating a sample into its constituents, said sample constituents eluting from an exit end of said column after separation;
    a flame detector comprising a flame jet apparatus adapted to withstand temperatures as high as 400° C., said flame jet apparatus having an interior mixing volume defining an interior surface wherein said exit end of said column is positioned and wherein said sample constituents eluting from said column are mixed with a fuel gas and are swept to an orifice communicating to the exterior of said flame jet apparatus into a flame;
    the interior surface of the mixing volume and the perimeter of the orifice being made of a highly inert ceramic material;
    whereby sample entering the column does not contact any metal surface before entering said flame.

8. The gas chromatography system of claim 7 wherein the flame jet apparatus further comprises a metal outer surface element whereby the flame jet apparatus may be used as a polarizing electrode.

9. The gas chromatography system of claim 7 wherein said ceramic material is high purity alumina.

10. The gas chromatography system of claim 8 wherein said metal outer surface is made of an alloy of nickel, cobalt and iron.

11. The gas chromatography system of claim 7 in which the ceramic material remains highly inert at temperatures as high as 500° C.

12. The gas chromatography system of claim 8 wherein said ceramic surfaces comprise at least one tubular ceramic element cemented to said metal outer surface element.

13. The gas chromatography system of claim 12 wherein a high purity alumina cement is used to cement said at least one tubular element to the metal outer surface member.

14. The gas chromatography system of claim 8 comprising a machined ceramic element nesting at least partially within and attached to the metal outer surface element.

15. The gas chromatography system of claim 14 wherein the ceramic element is attached to the metal element by brazing.

16. The gas chromatography system of claim 7 which has been treated by contacting the interior surface with a silylating reagent at an elevated temperature.

17. The gas chromatography system of claim 16 wherein the silylating treatment comprises passing dichlorodimethyl silane or N,O-bis-trimethylsilyl-trifluoroacetemide (BSTFA) through the flame jet apparatus at temperatures in excess of 400° C.

18. A flame detector for use in a gas chromatography system, comprising:

a flame jet apparatus having a hollow interior adapted for containing the sample eluting end of a chromatography column and an interior surface, the portion of the interior surface of said flame jet which is contacted by the sample eluting from the end of the chromatography column being made of a highly inert ceramic material, said flame jet apparatus further having a metal outer surface element and a machined ceramic element nesting at least partially within and attached to the metal outer surface element.

19. The flame detector of claim 18 wherein the ceramic element is attached to the metal element by brazing.

* * * * *